United States Patent [19]

Kankkunen et al.

[11] Patent Number: 5,003,981

[45] Date of Patent: Apr. 2, 1991

[54] IDENTIFICATION METHOD FOR THE CUFF SIZE IN A SPHYGMOMANOMETER AND FLOW RESTRICTION MEANS REQUIRED IN IDENTIFICATION

[75] Inventors: Lauri P. A. Kankkunen, Espoo; Raimo A. T. Piskunen, Vantaa; Börje T. Rantala, Helsinki, all of Finland

[73] Assignee: Instrumentarium Corporation, Finland

[21] Appl. No.: 376,984

[22] Filed: Jul. 6, 1989

[30] Foreign Application Priority Data

Jul. 8, 1988 [FI] Finland ............................... 883293

[51] Int. Cl.⁵ .............................................. A61B 5/02
[52] U.S. Cl. ..................................... 128/677; 128/686
[58] Field of Search ........................ 128/672, 677–686

[56] References Cited

U.S. PATENT DOCUMENTS 3,812,844 5/1974 Sokol ..................................... 128/686
4,501,280 2/1985 Hood, Jr. ............................. 128/677

*Primary Examiner*—Max Hindenburg
*Assistant Examiner*—J. P. Lacyk
*Attorney, Agent, or Firm*—Andrus, Sceales, Starke & Sawall

[57] ABSTRACT

The invention relates to an identification method for the cuff of a non-invasive automatic sphygmomanometer and to a flow restriction means for moderating the rate of pressure increase or decrease or both. Such a flow restriction means, which is fitted e.g. in a separate adapter (4), is useful particularly in connection with small-sized cuffs (6) intended for newborn babies. On the other hand, when using larger, such as adult cuffs, it is preferably to omit a flow restriction means completely. Identification is based on the fact that, when using a flow restriction means, either the increase of pressure downstream of a flow restriction means or the decrease of pressure upstream of a flow restriction means occurs slowly after the pumping is finished. If there is no flow restriction means at all, there will be no pressure change after the pumping is finished. Through the intermediary of a pressure sensing element (9), a control element (10) detects the size of a cuff.

A flow restriction means of the invention comprises one or a plurality of orifices through which the flow to cuff (6) must pass. The diameter and the length of such an orifice and the number of orifices are dependent on each other.

The abstract refers to FIG. 1.

27 Claims, 2 Drawing Sheets

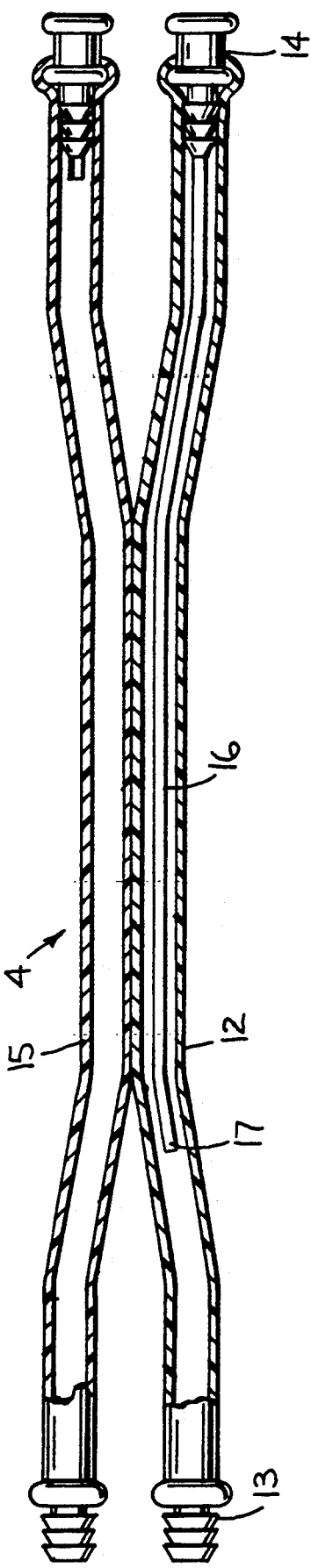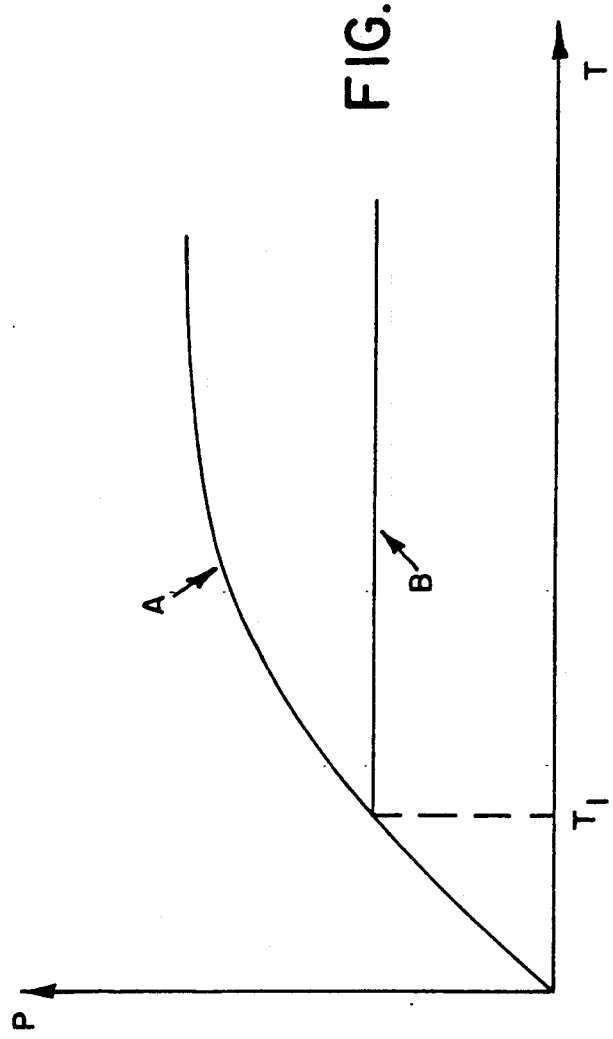

IDENTIFICATION METHOD FOR THE CUFF SIZE IN A SPHYGMOMANOMETER AND FLOW RESTRICTION MEANS REQUIRED IN IDENTIFICATION

BACKGROUND OF THE INVENTION

The present invention relates to an identification method for the cuff of a non-invasive automatic sphygmomanometer and to a flow restriction means required in the cuff size identification method for moderating the rate of pressure increase or decrease or both. This type of flow restriction means is particularly useful in connection with small-sized cuffs intended for newborn babies. However, when using larger, adult cuffs it is preferred that the flow restriction means be omitted completely or, if such a means is indeed needed, its gas or liquid through-flow must be sufficiently different from the flow restricting capacity of a flow restriction means used in connection with a smaller cuff. As a result of the generation of pressure occurring at the end of pumping, the size of a presently used cuff is identified.

In some equipment, the selection of cuffs intended for adults and newborn babies is effected by means of a selector switch provided on the device. Thus, the selector switch is used manually for selecting a mode of operation for the device depending on whether the question is about an adult or a newborn baby. There is however a hazardous possibility of forgetting to change the position of a selector switch when substituting e.g. an infant cuff for an adult one. Such a lapse might cause serious damage to newborn babies.

EP Patent application No. 122123 discloses a method developed for automatic identification of the size of a cuff. A certain pressure is pumped in the cuff followed by opening a valve for the reduction of cuff pressure. Opening of the valve generates a sonic pulse which travels along a tube to the cuff and further to a sensor which calculates the time between opening of the valve and arrival of the sonic pulse in the sensor. The arrival time of a sonic pulse in the sensor varies according to the size of a cuff. This delay time of a sonic pulse can be further modified by reducing the length of a tube leading to an infant cuff as compared to the length of a tube leading to an adult cuff. The delay time of a sonic pulse can be further cut down by fitting the tube leading from valve to cuff with a branch tube directly to the tube leading from cuff to sensor. On the basis of the delay time of a sonic pulse, a microprocessor detects whether the question is about an adult or an infant cuff.

In the cited EP Patent application, one problem in the solution based on a sonic pulse is that it is not possible to use tubes of arbitrary length leading from pressure transmission system to cuff since, in a program according to this system, a delay time is measured for the pulse and certain acceptable limits are set for that time. However, certain practical cases require tubes that should be either substantially shorter or longer in length than the tubes used in connection with the cited invention. The cuffs intended for adults and children may not be safely fitted with tubes of equal length as this may complicate the identification of the size of a cuff.

Another problem is also that, when a cuff is to be replaced with another one of different size, the entire long tube must also be replaced. The use of a short adapter cannot be managed.

A pipe linking the tube extending from pressure transmission system to cuff to the tube extending from cuff to sensor, said pipe cutting down the time used by a sonic pulse from valve to sensor, carries the disturbances caused by pumping and opening of the valve directly to the sensor. For this reason, the measuring accuracy suffers particularly in the case that cuff pressure control in the system is a continuous action.

Also known is a method, wherein a certain pressure is pumped in a cuff and, after reaching this pressure, the time taken up by pressure reduction is measured. This idea is based on the fact that the outflow of air is dependent on the size of a cuff. The longer the time taken up by outflow, the larger the cuff being used. A problem in this solution is the blocking of a cuff or a cuff tube, which in the worst case may lead to incorrect identification of the size of a cuff. Blocking of the tube can considerably lengthen the time taken up by the deflation of a cuff.

Attempts have been made to solve this last-mentioned problem by fitting the tube leading from pump and valve to cuff with a tubing which, in turn, is connected at its other end to the tube extending from cuff to pressure sensor and, thus, by-passing the cuff. This connecting tube, in turn, creates problems in connection with measurements by carrying the disturbances caused by pumping and opening of the valve to the pressure sensor. Measuring accuracy suffers especially in the case that cuff pressure control in the system is a continuous action.

The automatic identification of a cuff size can also be effected by measuring the time required for pumping a certain pressure in the cuff. Thus, the pumping time in connection with a larger cuff is longer than in the case of a smaller cuff. Problems in this type of solution include disturbances in the mains and variation of the pump characteristics which may lead to serious errors in the identification of a cuff.

SUMMARY OF THE PRESENT INVENTION

An object of this invention is to eliminate the above problems. Thus, the object is to provide a reliable automatic cuff identification method, which is independent of variations of the pump characteristics and disturbances of the mains and which allows the use of tubes of arbitrary length that need not be necessarily replaced when substituting a cuff of different size. Another object is to use a flow restriction means to provide a measuring or testing system reducing the disturbances caused by the opening or closing of a valve or valves as well as to intensify the pressure pulses on a cuff detectable by means of the pressure testing system.

The characterizing features of a cuff size identification method of the invention and a flow restriction means required in the identification are set forth in the annexed claims.

BRIEF DESCRIPTION OF THE DRAWINGS

The invention will now be described in more detail with reference made to the accompanying drawings, in which FIG. 4 shows the adapter of FIG. 3 along a section A—A, FIG. 5 shows the principle applied in an identification method of the invention for distinguishing two cuffs of different size from each other.

DETAILED DESCRIPTION OF THE PREFERRED EMBODIMENTS

Figure 1:
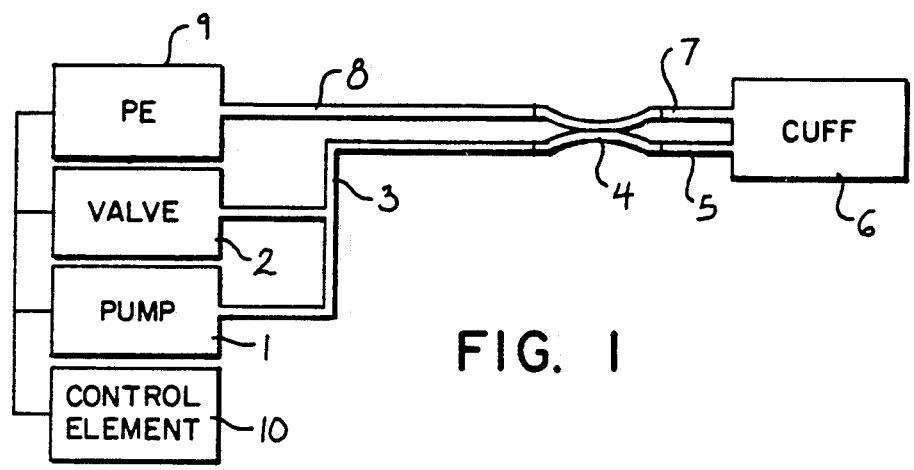
FIG. 1 shows a diagrammatic view of an apparatus used in a cuff size identification method of the invention and provided with a cuff intended for the newborn.

FIG. 1 shows diagrammatic a view of an apparatus used in the cuff size identification method. In the case illustrated in this figure, blood pressure is tested or measured on a newborn baby. A tube 3 extends from a pump 1 and a valve 2 to an adapter 4 with a tube 5 extending further to a cuff 6. On the other hand, a tube 7 leads from the cuff to adapter 4 with a tube 8 extending further to a pressure sensing element 9. The operation of valve 2 and pump 1 is governed by a control element 10, preferably a microprocessor. The control element 10 operates on the basis of a test reading received from pressure sensing element 9. The control element is also capable of identifying a cuff type on the basis of a piece of information received from pressure sensing element 9.

Figure 2:
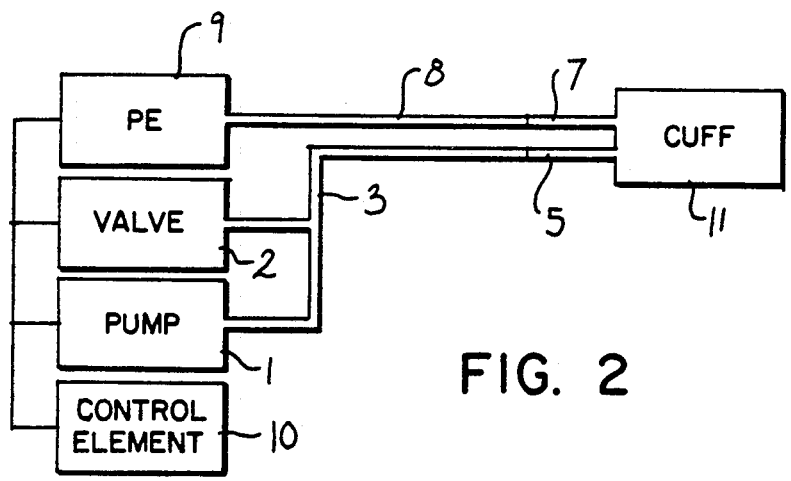
FIG. 2 shows a diagrammatic view of an apparatus used in a cuff size identification method of the invention and provided with a cuff intended for adults.

FIG. 2 shows a diagrammatic view of an apparatus used in the cuff identification method when the question is about testing blood pressure in adults. The only difference from FIG. 1 is the absence of an adapter 4 and the adult cuff 11 is directly connected to tubes 3 and 8 through the intermediary of cuff tubes 5 and 7.

Figure 3:
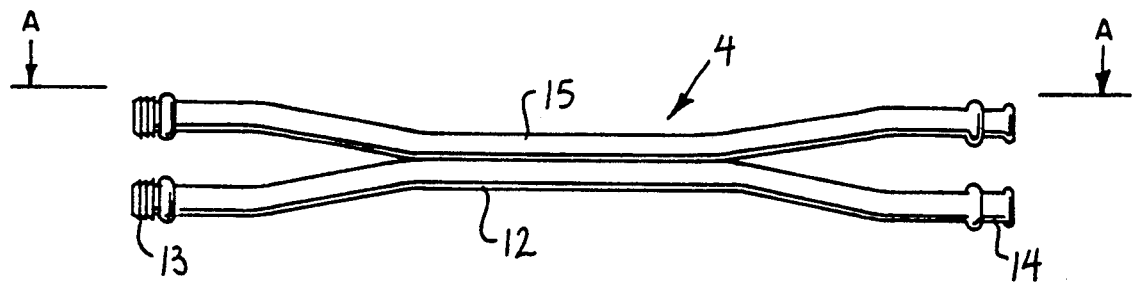
FIG. 3 shows a separate adapter of the invention that can be fitted on a tube leading to the cuff.

An adapter 4 is shown in more detail in FIGS. 3 and 4. A tube 12 included in adapter 4 is thus attached by means of a fastener 13 or 14 to a conventional tube 3 extending from valve 2 and pump 1 to cuff 6. To the other end of adapter tube 12 is attached a cuff 6 by means of available fastener 13 or 14 through the intermediary of tube 5. Between the tubes 7 and 8 leading from cuff 6 to pressure sensing element 9 said adapter 4 is also fitted with a tube 15. Inside said adapter tube 12 is a liquid or preferably gas flow restricting means 16 provided with an orifice 17 for discharging the gas or liquid. This means is preferably tubular in design. The diameter of a flow restriction means can be the greater, the longer said means 16 is and, naturally, vice versa. Thus, said means 16 must restrict the flow of gas or liquid sufficiently, so that control element 10 would be capable, on the basis of test readings received from pressure sensing element 9, of detecting with sufficient distinction the pressure differences prevailing in cuffs 6 and 11 for distinguishing cuffs of different sizes from each other.

FIG. 5 illustrates the significance of a flow restriction means 16 (curve A) and the absence of such means (curve B) in a situation, wherein air is pumped into cuffs 6 and 11. In FIG. 5, pressure is depicted as a function of time. Prior to the identification of a cuff, a pressure of e.g. 20–30 mmHg is rapidly pumped into the system with pump 1. In FIG. 5, the pumping is stopped at a moment $T_1$. As shown in the figure, the pressure increases downstream of a flow restriction means (curve A) slowly after the pumping is stopped and only after a certain period of time the equalization of pressures occurs through a flow restriction means. In case no flow restriction means is used (curve B), the increase of pressure in cuff 11 stops without any significant delay right at the end of pumping. The control element 10 observes the difference indicated by curves A and B.

The detection of a pressure difference is preferably effected in practice e.g. by comparing the pressure prevailing at the end of pumping either with a pressure change following the stoppage of pumping up to pressure equalization or possibly with a pressure prevailing after a given time interval or time intervals from the stoppage of pumping. Thus, the presence of a flow restriction means can be verified by means of a single pressure pulse only, but of course a plurality of pulses can be used to be on the safe side.

A control element 10 adapts actions of the apparatus to comply with a small-sized cuff 6 provided it detects the presence of a flow restriction means. In the case of an infant cuff 6, a pressure pumped in the cuff shall remain lower than that applied in the case of an adult cuff 11. The size of a cuff is preferably observed also when relieving pressure from a cuff.

A flow restrictor divides a pneumatic system in two sections. Thus, the rapid pressure changes occurring between a flow restriction means and a pressure control system appear in a more subdued form in the section of a system between flow restriction means 16 and pressure sensing element 9.

Hence, a flow restriction means 16 prevents the development of disturbances when the cuff pressure is continuously reduced by opening and closing one or a plurality of valves. Similarly, a flow restriction means 16 thus prevents the passage of disturbances to a cuff and to a pressure sensing element when pumping in a gas or a liquid. An important aspect is definitely that a flow restriction means also intensifies pressure pulses detected by a pressure sensing element and applied to a cuff, this being particularly important in connection of blood pressure testing in newborn babies because of a small volume of a cuff intended for infants. Thus, a flow restriction means serves as a reducer of the dead zone in a long tube.

In order not to attach a larger cuff to an adapter 4 fitted with a flow restriction means 16, it is preferable to provide adapter 4 with such an attachment which is only compatible with small-sized cuffs.

In addition to the solutions disclosed in FIGS. 1 and 2, it is possible to adapt a pressure sensing element 9 to sense or monitor the development of pressure occurring between pump 1 and flow restriction means 16 or between pump 1 and a cuff after the pumping is finished. When using a flow restriction means, the condition will be opposite to that shown in FIG. 5, i.e. after the pumping is stopped, the pressure between pump and flow restriction means will decrease. On the other hand, the pressure remains unchanged at the end of pumping as in FIG. 5 if there is no flow restriction means. A control element identifies the size of a cuff on the basis of the received data.

Of course, a flow restriction means 16 fitted in the adapter can be considerably different from the solution shown in FIG. 4. Instead of a single tube or line there may be a plurality of tubes or lines either in parallel or in succession. Also e.g. an apertured plate or disc, which thus includes one or a plurality of orifices, is a suitable flow restriction means. Quite possibly a flow restriction means 16 may consist merely of flow blocking barriers, such as membrane-like strips or sort of brushes which restrict the movements of a gas or a liquid in orifice 17 or tubes 3, 4 or 5. These are a few possible solutions but others exist as well. An identification method of the invention is by no means limited to preferred throttle or restrictor designs presented in connection with the invention. After all, the main objective is the ability to restrict a flow between a cuff and a pressure transmission system.

Neither is a separate adapter absolutely necessary as a flow restriction means 16 can also be fitted in a tube 5 leading to cuff 6 or even in the actual cuff 6 or also in a tube 3. A flow restricting tube or line need not necessarily be fitted inside any tube, e.g. an adapter, but it can be a section of a tube leading from a pump or a valve to a cuff.

In the solutions described in connection with the drawings, reference is primarily made to the identification of a cuff intended for adults and for newborn babies. Of course, the identification possibilities are not limited to different size cuffs but this identification system is applicable also to the identification of cuffs of other sizes. If necessary, this system can also be applied to the identification of more than two different size cuff types.

FIGS. 1 and 2 illustrate that a single common tube 3 extends from pump 1 and valve 2 to a cuff. Valve 2 and pump 1 each may of course have their own tube leading directly to a cuff. In this case, a flow restriction means 16 must be fitted at least in a tube between a pump and a cuff when the question is about a smaller cuff, but possibly also in a tube leading from a valve to a cuff.

The number of elements set forth in diagrammatic views 1 and 2, such as valves, can of course be more than one. It is also obvious that tubes 5 and 7 attached to a cuff are not necessarily required provided that an adapter 4 or tubes 3 and 8 can be attached directly to a cuff.

A pressure pumped in connection with the cuff size identification may quite well differ from the 20–30 mmHg level mentioned in reference to the drawings.

We claim:

1. Apparatus for identifying a cuff coupled to a sphygmomanometer by connection means, said sphygmomanometer having means for creating a change in the pressure of a fluid in the connection means and having means for sensing fluid pressure phenomena in the connection means, said apparatus comprising:
   means operatively associated with the cuff and insertable in the connection means when the cuff is connected to the sphygmomanometer for restricting transfer of fluid pressure changes between a first portion of the connection means and a second portion of the connection means, whereby the sensing means can identify the cuff by means of the fluid pressure phenomena resulting from the presence of the restricting means in the connection means.

2. The apparatus according to claim 1 wherein said restricting means is further defined as means for restricting fluid flow in the connection means.

3. The apparatus according to claim 2 wherein said fluid flow restricting means is further defined as orifice means.

4. The apparatus according to claim 3 wherein said orifice means forms a portion of a tube positioned in the connection means.

5. The apparatus according to claim 4 wherein the properties of the orifice means and the length of the tube are selected in accordance with their mutual dimensions for providing desired fluid flow restricting properties.

6. The apparatus according to claim 3 wherein said orifice means is located in a plate positioned in the connection means.

7. The apparatus according to claim 3 wherein said orifice means includes a plurality of orifices.

8. The apparatus according to claim 7 wherein said orifice means includes a plurality of parallel orifices.

9. The apparatus according to claim 7 wherein said orifice means includes a series of orifices.

10. The apparatus according to claim 1 wherein said restricting means is inserted between the cuff and the sphygmomanometer means for creating a fluid pressure change in the connection means.

11. The apparatus according to claim 1 wherein said restricting means is connected to said cuff.

12. The apparatus according to claim 1 wherein said restricting means is located in a coupling for connection the cuff to the connecting means.

13. The apparatus according to claim 12 wherein said coupling is formed to be compatible only with the cuff to be identified.

14. A method for identifying a cuff coupled in fluid communication to a sphygmomanometer by connection means, said method comprising the steps of:
   creating a change in the pressure of the fluid in a first portion of the connection means;
   restricting transfer of the fluid pressure change between the first portion and a second portion of the connection means when a first cuff is coupled to the sphygmomanometer, but not when a second cuff is coupled to the sphygmomanometer; and
   sensing fluid pressure phenomena in the connection means to determine whether pressure change transfer in the connection means is restricted and to identify whether the first or second cuff is coupled to the sphygmomanometer.

15. The method according to claim 14 wherein the sensing step is further defined as sensing pressure levels existing in the connection means.

16. The method according to claim 15 wherein the sensing step is further defined as comparing a pressure level existing in the connection means with a reference pressure level.

17. The method according to claim 14 wherein the sensing step is further defined as sensing pressure change phenomena occurring in the connection means.

18. The method according to claim 14 wherein the pressure change creation step is further defined as increasing the fluid pressure in the first portion of the connection means.

19. The method according to claim 14 wherein the pressure change creation step is further defined as reducing the fluid pressure in the first portion of the connection means.

20. The method according to claim 14 wherein the pressure change transfer restricting step is further defined as restricting fluid flow between the first portion and the second portion of said connection means.

21. The method according to claim 14 wherein the pressure phenomena sensing occurs in the second portion of the connection means.

22. The method according to claim 14 wherein the pressure phenomena sensing occurs in the first portion of the connection means.

23. The method according to claim 18 further defined as increasing the fluid pressure in the first portion of the connection means by a source of fluid pressure and wherein the pressure change transfer restriction occurs between the source of fluid pressure and the cuff to be identified.

24. The method according to claim 18 further defined as decreasing the fluid pressure in the first portion of the connection means by a pressure reducing means and wherein the pressure change transfer restriction occurs between the pressure reducing means and the cuff to be identified.

25. The method according to claim 20 further defined as restricting the fluid flow by means of at least one orifice means.

26. The method according to claim 25 wherein the orifice means occurs in conjunction with a tube within the connection means and wherein the properties of the orifice means and the length of the tube are selected in accordance with their mutual dimensions for providing the desired fluid flow restriction.

27. The method according to claim 14 further defined as identifying whether an adult cuff or an infant cuff is coupled to the sphygmomanometer and wherein pressure change transfer is restricted when the infant cuff is coupled to the sphygmomanometer.

* * * * *